United States Patent [19]

Felder et al.

[11] 4,348,377

[45] Sep. 7, 1982

[54] NEW DERIVATIVES OF 2,4,6-TRIIODO-ISOPHTHALIC ACID, PROCESES FOR THEIR SYNTHESIS AND X-RAY CONTRASTING MATERIALS CONTAINING THESE

[75] Inventors: Ernst Felder, Vitale, Switzerland; Davide Pitre, Milan, Italy

[73] Assignee: Bracco Industria Chimica S.p.A., Milan, Italy

[21] Appl. No.: 173,765

[22] Filed: Jul. 30, 1980

[30] Foreign Application Priority Data

Aug. 9, 1979 [IT] Italy ............................. 25027 A/79

[51] Int. Cl.$^3$ ............................................. A61K 49/04
[52] U.S. Cl. .......................................... 424/5; 564/153
[58] Field of Search ............................. 424/5; 564/153

[56] References Cited

U.S. PATENT DOCUMENTS

| | | | |
|---|---|---|---|
| 3,632,738 | 1/1972 | Ingelman | 424/5 |
| 3,678,152 | 7/1972 | Bjork et al. | 424/5 |
| 4,239,747 | 12/1980 | Pfeiffer et al. | 424/5 |
| 4,250,113 | 2/1981 | Nordal et al. | 564/153 |

FOREIGN PATENT DOCUMENTS 2457789  6/1975  Fed. Rep. of Germany .......... 424/5

*Primary Examiner*—Delbert R. Phillips
*Attorney, Agent, or Firm*—Toren, McGeady & Stanger

[57] ABSTRACT

Novel, radio-opaque compounds comprising water-soluble bis-[N-{3,5-bis-(hydroxyalkylaminocarbonyl)-2,4,6-triiodo-phenyl}-N-(α-hydroxyacyl)-amino]-alkanes are disclosed for use as X-ray contrast agents. These compounds are relatively simple to synthesize, possess low toxicity and have good stability as well as resistance to hydrolysis. Methods for preparation and use of the compounds are also disclosed.

7 Claims, No Drawings

NEW DERIVATIVES OF 2,4,6-TRIIODO-ISOPHTHALIC ACID, PROCESSES FOR THEIR SYNTHESIS AND X-RAY CONTRASTING MATERIALS CONTAINING THESE

BACKGROUND OF THE INVENTION

1. Field of the Invention

The present invention relates to novel, readily water-soluble bis[N-{3,5-bis-(hydroxyalkylaminocarbonyl)-2,4,6-triiodo-phenyl}-N-(α-hydroxyacyl)-amino]-alkanes for use as X-ray contrasting agents.

2. Description of the Prior Art

5-Acylamino-2,4,6-triiodo-isophthalic acid diamides and their use in X-ray contrasting materials is disclosed in Swiss Pat. No. 544,551. The compounds contain only simple, unsubstituted aliphatic acyl groups, generally acetyl groups. Certain members of this class of compounds which contain carbohydrate residues possess sufficient water-solubility, for example, 3-acetylamino-N-methyl-acetylamino-2,4,6-triiodo-benzoyl-glucosamine which has become known under the international non-proprietary name of METRIZAMIDE. In this connection, see also compound No. 11 of U.S. Pat. No. 3,701,771, British Pat. No. 1,321,591, Swiss Pat. No. 544,551, Austrian Pat. No. 318,134 and German Offenlegungsschrift No. 2,031,724, as well as publications of T. Almen, S. Salvesen, K. Golman: Acta Radiologia Suppl. 335 (1973), pages 1–13, 233–75, and 312–38. A disadvantage of this compound is that it is difficult to synthesize and particularly, that it is relatively unstable. This limits significantly its usability and makes the handling of the material difficult.

1-5-α-hydroxypropionylamino-2,4,6-triiodo-isophthalic-acid-bis-(1,3-dihydroxyisopropylamide), known under the international non-proprietary name of IOPAMIDOL, represents an advance over this art. In this connection, see also German Pat. No. 2,547,789, British Pat. No. 1,472,050, U.S. Pat. No. 4,001,323 and the article by Felder et al., IL FARMACO, Ed. Sc. 32, 835–844 (1977). This compound is distinguished by an essentially simpler structure, by higher stability, by being easier to isolate and by a relatively lower viscosity of its concentrated aqueous solutions. The toxicity of this compound is very low.

Developments in recent years have shown clearly that it is extremely difficult and only infrequently possible to find non-ionic compounds which have the specific properties required for the individual techniques of X-ray contrast investigations. These required properties are a true water-solubility, sufficient for producing stable, that is, not supersaturated, concentrated solutions, maximum general and neurotropic tolerance, minimum osmolality, a relatively high viscosity which can be matched for the specific end use, a maximum stability towards hydrolytic effects, and a structure which is sufficiently simple to make its synthesis economically feasible as well as to simplify its isolation and purification.

SUMMARY OF THE INVENTION

We have discovered a group of radio-opaque compounds which possess the above-enumerated desirable properties. These compounds have the formula:

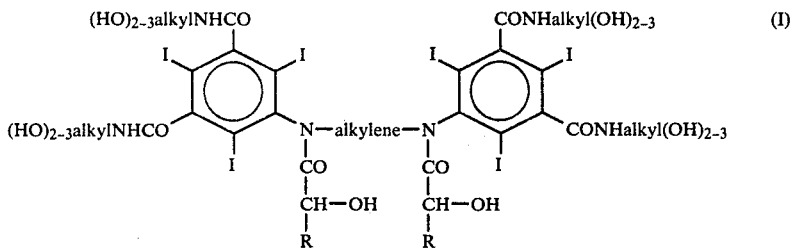

in which $(HO)_{2-3}$alkyl is 1,3-dihydroxyisopropyl, 2,3-dihydroxypropyl or 1,3-dihydroxy-2-hydroxy-methylisopropyl, R is hydrogen or methyl, and alkylene is a bivalent alkylene residue with 2 to 10 carbon atoms, i.e., $-(CH_2)_{2-10}-$, which may be substituted by hydroxy functions, or a mono-, di- or polyoxaalkylene residue with 4 to 12 carbon atoms, i.e., $-(C_nH_{2n})_{0-4}-O-C_nH_{2n}-$ wherein n is 2 or 3 which may be substituted by hydroxy functions.

We have also discovered a process for synthesis of these compounds as well as non-ionic X-ray contrasting materials, which are suitable especially for vasography, urography, bronchography and for visualizing body cavities and fluid spaces and which contain the aforementioned compounds as radio-opaque components.

The process of synthesizing bis-[N-{3,5-bis-(hydroxyalkylaminocarbonyl)-2,4,6-triiodo-phenyl}-N-(α-hydroxyacyl)-amino]-alkanes of formula I which can be used as radio-opaque components in X-ray contrasting materials, is characterized by the fact that a 5-α-hydroxyacylamino-2,4,6-triiodo-isophthalic-acid-bis(dihydroxypropylamide) of the general formula (III)

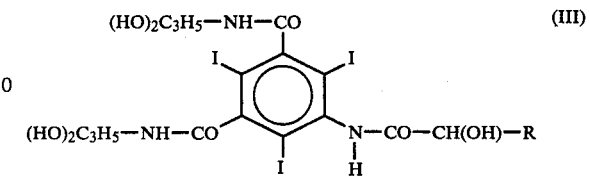

is alkylated at the aromatic nitrogen atom by a reaction with alkylating materials of the general formula (IV)

in which

R and alkylene in formulas (III) and (IV) have the same meaning as in formula I, and X represents a halogen atom, iodine, bromine, or chlorine or a sulfate or a sulfonate radical ($-OSO_2-OR_1$ or $-OSO_2-$alkyl or $-OSO_2-$aryl).

The compounds of the present invention are generally distinguished by a high water solubility, which reaches absolute peak values in the case of some representatives, by optimum tolerance and especially by their slight osmolality. Additionally, the compounds exhibit consistently high stability, especially towards hydrolytic effects which stability even clearly exceeds the good hydrolytic stability of the starting materials on which they are based and which are not alkylated at the aromatic nitrogen atom. This enhanced stability towards hydrolytic effects is important for preventing even a trace formation of free aromatic amines which might be associated with a possible, but unacceptable cytotoxic effect of these amines in conjunction with X-rays. In this connection, see also: A. Norman et al., Radiology 129, 199–203 (Oct. 1978).

DESCRIPTION OF THE PREFERRED EMBODIMENT

It is particularly surprising and, at the same time, valuable that the water solubility of the basic compound, for example, of the 5-hydroxyacetylamino-2,4,6-triiodo-isophthalic-acid-bis-(2,3-dihydroxypropylamide) can at times be improved appreciably by linking two triiodo-isophthalic acid amide molecules by means of an alkylene bridge attached to the respective aromatic nitrogen atoms.

With reference to the structure of the inventive compounds, examples of unsubstituted alkylene residues, which connect the two triiodo-isophthalic acid amide molecules, are ethylene, propylene, butylene, pentylene, hexylene, octylene, nonylene, and decylene. In general, alkylene residues with 3 or more carbon atoms are preferred, because these are introduced more easily.

In order to enhance the hydrophilic character of the compounds, oxygen atoms may be incorporated into the alkylene bridges which hold the two halves of the molecule together. This may be accomplished by interrupting the hydrocarbon chain after every 2 and usually after every 2 to 3 carbon atoms by an oxygen atom.

Examples of such oxygen-containing alkylene bridges are:

$$-CH_2CH_2-O-CH_2CH_2-,$$

$$-CH_2CH_2-O-CH_2CH_2-O-CH_2CH_2-,$$

$$-CH_2CH_2-O-CH_2CH_2-O-CH_2CH_2-O-CH_2CH_2-,$$

$$-CH_2CH_2-(O-CH_2-CH_2)_3-O-CH_2CH_2-,$$

$$-CH_2CH_2-O-CH_2-CH_2-CH_2-O-CH_2CH_2-,$$

$$-CH_2CH_2CH_2-O-CH_2CH_2-O-CH_2CH_2-,$$

$$-CH_2CH_2CH_2-O-CH_2CH_2CH_2-, \text{ etc.}$$

The substitution for hydroxyl functions for the individual hydrogen atoms of the alkylene bridge, as a result of which the following alkylene residues, for example, are formed, serves the same purpose:

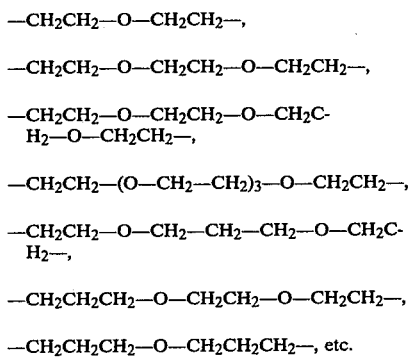

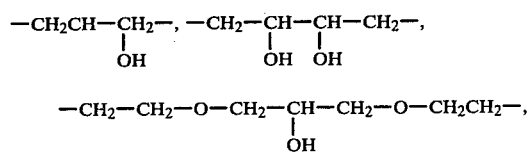

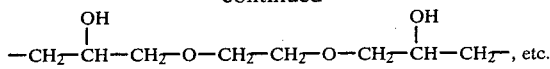

The inventive compounds are distinguished by a greatly reduced osmolality and usually by an increased viscosity, which is very desirable for many application purposes, especially for myelography as well as, for example, for certain investigations of cardiac valves, for visualizing body cavities, for bronchography, hysterosalpingography, arthrography and lymphography.

The main area of application of the present novel X-ray contrasting materials is in the field of neuroradiology, especially the visulization of hollow spaces which contain the cerebrospinal fluid. These spaces consist of different cavities which are connected with the central nervous system. They comprise, for example, the ventricle of the brain, the cisternae, the subarachnoid space around the brain as well as the spinal canal. The radiological investigation of these cavities usually is subdivided into three main groups, ventriculography, cisternography and myelography. Myelography is the radiological investigation of the spinal subarachnoid space.

Compared to material administered intravenously, the tolerance for the contrasting materials, which are introduced into these spaces, is decreased very considerably. The sensitivity towards these materials is increased, the closer one approaches the brain. The various areas, however, are in communication with each other, so that transfer from one area to the neighboring, possibly more sensitive area, is possible. A main objective of the X-ray inspections is the determination of space-narrowing processes, perhaps in the spinal canal, and the clarification of disfunctions resulting from the absence of or defective communication. An important examination, but one which is particularly difficult and burdensome for the patient, is the examination of the cavity system of the brain itself.

Of particular importance are the physical and chemical properties, which are demanded for contrasting materials, such as, a matching viscosity to facilitate the application, but also to prevent premature drainage from the cavities which are to be visualized, and the correct osmolality for preventing osmotic processes to a large extent. The contrasting materials should not, however, remain in the spinal canal for too long a period, as has been the case with the previously used water-insoluble, slowly metabolized, iodinated oils. Finally, the tolerance requirements for X-ray contrasting materials are understandably particularly high in neuroradiology. Compared to the amount of fluid in the inspection space, the amounts of contrasting material are large.

The inventive compounds fulfill the conditions which have been placed on them in an optimum manner. They are so viscous that they remain in the inspection space for a period of time which is sufficient for an X-ray inspection to be carried out reliably. Because of their water-solubility and their miscibility with the cerebrospinal fluid, they do not, however, remain at the injection site over long periods. Because of their chemical stability, they are not metabolized but are eliminated essentially unchanged through the kidneys. As nonionic contrasting materials with a matched osmotic pressure of their solutions of slight electrical conductivity, their effect on the nervous conduction system is reduced and their use is therefore less painful.

In the process of the present invention, an appropriate 5-α-hydroxyacylamino-2,4,6-triiodo-isophthalic-acid-bis-(dihydroxypropylamide) is reacted in the presence of bases with an alkylene disulfonate, for example, a bis-(methane, benzene or toluene-sulfonyloxy)-alkane.

Typical examples of alkylating materials of formula X-alkylene-X are: 1,2-diiodethane, 1,2-dibromomethane, 1,2-dichloroethane, 1,3-dichloropropane, 1,3-diiodopropane, 1,4-dibromobutane, 1,5-diiodopentane, 1,6-diiodohexane (hexamethylene diiodide), 1,7-dibromoheptane, 1,8-diiodooctane, 1,9-dibromononane, 1,10-diiododecane, 1,5-dichloro-3-oxa-pentane, 1,5-diiodo-3-oxa-pentane, 1,8-dibromo-3,6-dioxa-octane, 1,11-diiodo-3,6,9-trioxa-undecane, 1,14-dibromo-3,6,9,12-tetraoxa-tetradecane, 1,9-diiodo-3,7-dioxa-nonane, 1,10-dibromo-4,7-dioxa-decane, 1,7-dibromo-4-oxaheptane, 1,4-dibromo-2,3-bis-(acetoxy)-butane, 1,4-dibromo-2,3-iodopropylidene-dioxybutane, 1,3-dibromo-2-hydroxypropane, 1,3-diiodo-2-acetoxypropane, 1,9-dibromo-3,7-dioxa-5-acetoxy-nonane, 1,10-diiodo-4,7-dioxa-2,9-bis-(acetoxy)-decane, 1,3-bis-(methanesulfonyl-oxy)-2-acetoxy-propane, 1,2-bis-(4-toluenesulfonyloxy)-ethane, 1,3-bis-(methanesulfonyloxy)-propane, 1,4-bis-(4-toluenesulfonyloxy)-butane, 1,5-bis-(benzenesulfonyloxy)-butane, 1,16-bis-(methanesulfonyloxy)-4,7,10,13-tetraoxahexadecane, 1,3-bis-(methoxysulfonyloxy)-propane and 1,4-bis-(ethoxysulfonyloxy)-butane.

If alkylene bridges, which contain free hydroxy functions are introduced, it is frequently advisable to mask the hydroxy function by acylation with a lower fatty acid, such as, for example, acetic acid or, in the case of two or more hydroxy functions, by acetal or ketal formation, for example, with acetone. After the reaction with the appropriate 5-acylamino-2,4,6-triiodo-isophthalic-acid-diamide has been accomplished, the hydroxyl function can be liberated by hydrolysis. Alkalis can be used for this purpose in the case of acyl derivatives, and acids in the case of acetal and ketal derivatives.

The strong acid (2×HX) which is released during the alkylation with X—alkylene—X, is neutralized by the base present.

Compounds, suitable for use as bases are, for example, strong alkalis, such as, alkali alcoholates (NaOMe, NaOEt, KOMe, KOEt, KiOMe, LiOEt), alkali hydroxides (NaOH, KOH, LiOH), alkali carbonates ($Na_2CO_3$, $K_2CO_3$), quaternary ammonium hydroxides (tetramethylammonium hydroxides). The reaction is usually carried out in a polar solvent, such as, for example, water, lower alcohols (MeOH, EtOH, ethylene glycol, propylene glycol, glycerin), lower glycol ethers (methoxy ethanol, ethoxy ethanol, butyloxy ethanol), ketones (acetone, methyl ethyl ketone, methyl isopropyl ketone, methyl isobutyl ketone) or in decidedly aprotic solvents, such as, for example, hexametapol (MPT), dimethylformamide (DMF), dimethylacetamide (DMAC), dimethylsulfoxide (DMSO) or in solvent mixtures. The reaction is accelerated by heat.

The reaction proceeds via the following general sequence:

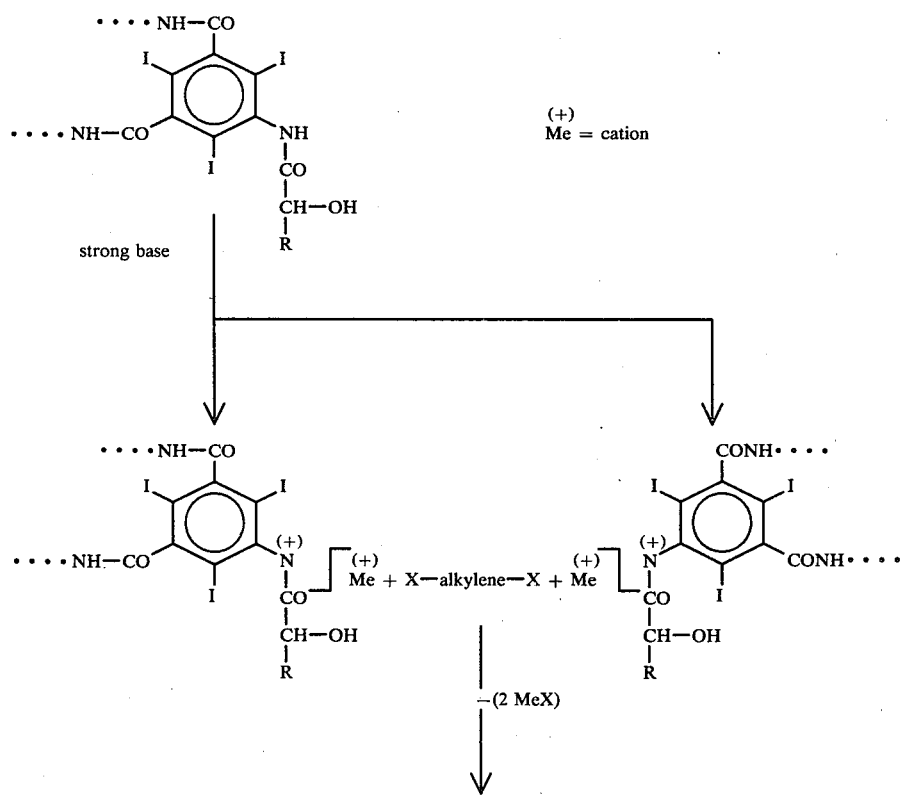

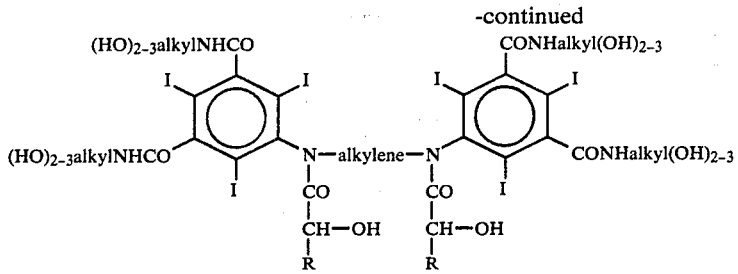

-continued

The following examples illustrate the present invention:

EXAMPLE 1

1,6-bis-[N-{3,5-bis-(1,3-dihydroxyisopropylaminocarbonyl)-2,4,6-triiodo-phenyl}-N-(1-α-hydroxypropionyl)-amino]-hexane Formula II: $(HOH)_2C_3H_5 = (HOCH_2)_2CH$, $R = -CH_3$, alkylene $= -(CH_2)_6-$ A solution of 58.3 g of 1-5-α-hydroxypropionyl-amino-2,4,6-triiodo-isophthalic-acid-bis-(1,3-dihydroxyisopropylamide) (IOPAMIDOL) (0.075 moles) in 200 ml of water is treated with exactly the stoichiometric amount (0.075 moles) of 2 N sodium hydroxide. The solution has a pH of 11.9. It is evaporated to dryness under vacuum. The residue, consisting of the 5-N sodium compound (sodium salt) of 1-5-α-hydroxypropionylamino-2,4,6-triiodo-isophthalic-acid-bis-(1,3-dihydroxyisopropylamide) is dried under vacuum at 100° C.

Equivalent weight of $C_{17}H_{21}I_3N_3NaO_8$— calc. 799.27, found 799.08.

The sodium salt (60 g=0.075 moles) so obtained, is dissolved in 180 ml of dimethylacetamide (DMAC) and treated dropwise at 30° C. with 12.8 g of hexamethylene iodide (0.037 moles) and stirred at 45°–50° C. until the reaction is completed.

The reaction solution is evaporated under vacuum. The oily residue is mixed with 300 ml of methylene chloride. The precipitate formed is filtered off, washed repeatedly with absolute ethanol, dissolved in 250 ml of water and desalinated with the help of ion-exchange resins and subsequently purified further by percolation through a column of absorbent resin (agglomerates of styrene polymers).

The eluate is evaporated. The oily residue crystallizes on treatment with boiling ethanol.

Yield: 50 g of 1,6-bis-[N-{3,5-bis-(1,3-dihydroxyisopropylaminocarbonyl)-2,4,6-triiodo-phenyl}-N-(1-α-hydroxypropionyl)-amino]-hexane, that is 81% of the theoretical yield.

Melting point: 285°–290° C. (softens at 195° C.)

TLC: $R_f=0.20$; 0.30 and 0.41. Solvent —$CH_2Cl_2$/MeOH=2:1.

$C_{40}H_{54}I_6N_6O_{16}$: I calc. 46.53% found 46.35%.

$[\alpha]_D^{20} = +13.93°$ $[\alpha]_{436}^{20} = +34.04°$ (c=1% in water).

Water solubility: $\geq 100\%$ (w/v) at 25° C.

EXAMPLE 2

1,7-bis-[N-{3,5-bis-(1,3-dihydroxyisopropylaminocarbonyl)-2,4,6-triiodo-phenyl}-N-(1-α-hydroxypropionyl)-amino]-heptane Formula II: $(HO)_2C_3H_5=(HOCH_2)_2CH$, $R=-CH_3$, alkylene$=-(CH_2)_7-$ A solution of 80 g of the sodium salt of IOPAMIDOL (0.1 mole) in 180 ml of DMAC is reacted with 17.6 g of 1,7-diiodoheptane (0.05 moles) and worked up as described in Example 1.

The crude product, desalinated with ion-exchange resins, is purified further by countercurrent distribution (liquid-liquid extraction) between water (10×400 ml) and n-butanol (10×400 ml).

Melting point: ca. 220° C.

TLC: $R_f=0.14$ and 0.19. Solvent —$CH_2Cl_2$/MeOH=2:1.

$C_{41}H_{56}I_6N_6O_{16}$: I calc. 46.14% found 46.34%.

$[\alpha]_{436}^{20}=38°$ (c=5% in water).

Water solubility: 20% (w/v) at 20° C., 100% (w/v) at the boiling point.

EXAMPLE 3

1,9-Bis-[N-{3,5-bis-(1,3-dihydroxyisopropylaminocarbonyl)-2,4,6-triiodo-phenyl}-N-(1-α-hydroxypropionyl)-amino]-nonane Formula II: $(HO)_2C_3H_5 -= (HOCH_2)_2CH-$, $R=-CH_3$, alkylene$=-(CH_2)_9$ A solution of 90 g of the sodium salt of IOPAMIDOL (0.112 moles) in 200 ml of DMAC is reacted with 21.4 g of 1,9-diiodononane (0.0564 moles) at 20°–30° C. and worked up as described in Example 2.

The title compound obtained melts at about 230° C. (with decomposition).

TLC: $R_f=0.19$ and 0.26 Solvent —$CH_2Cl_2$/MeOH=2:1.

$C_{43}H_{60}I_6N_6O_{16}$: I calc. 45.36% found 45.34%.

$[\alpha]_{436}^{20}>44°$ (c=2% in water).

Water solubility: 40% (w/v) at 25° C.

EXAMPLE 4

1,7-bis-[N-{3,5-bis-(1,3-dihydroxyisopropylaminocarbonyl)-2,4,6-triiodo-phenyl}-N-hydroxyacetyl-amino]-heptane Formula II: $(HO)_2C_3H_5=(HOCH_2)_2CH-$, $R=-H$, alkylene$=-(CH_2)_7-$ The sodium salt of 5-hydroxy-acetylamino-2,4,6-triiodo-isophthalic-acid-bis-(1,3-dihydroxyisopropylamide) (51 g, 0.065 moles), prepared from the free compound by reaction with the equivalent amount of sodium methylate in methanol, is reacted in methanol or methoxymethanol (150–200 ml) with 11.5 g of 1,7-diiodoheptane (0.0325 moles).

Yield: 35 g of 1,7-bis-[N-{3,5-bis-(1,3-dihydroxyisopropylaminocarbonyl)-2,4,6-triiodo-phenyl}-N-hydroxyacetyl-amino]-heptane, that is, 66% of the theoretical yield.

Melting point: 285°–290° C. with decomposition.
TLC: $R_f$=0.05. Solvent —CH$_2$Cl$_2$/MeOH=2:1
TLC: $R_f$=0.04. Solvent CHCl$_3$/MeOH/NH$_4$OH (25%)=6:3:1.
C$_{41}$H$_{56}$I$_6$N$_6$O$_{16}$: I calc. 46.92% found 46.70%
Water solubility: 20% (w/v) at 25° C., 100% at the boiling point.

EXAMPLE 5

1,9-bis-[N-{3,5-bis-(1,3-dihydroxyisopropylaminocarbonyl)-2,4,6-triiodo-phenyl}-N-hydroxyacetyl-amino]-nonane Formula II: (HO)$_2$C$_3$H$_5$—=(HOCH$_2$)$_2$CH—, R=—H, alkylene=—(CH$_2$)$_9$—

The sodium salt of 5-hydroxyacetylamino-2,4,6-triiodo-isophthalic-acid-bis-(1,3-dihydroxyisopropylamide) (44 g), prepared from the free compound by reaction with the equivalent amount of sodium methylate in methanol, is reacted in methanol, methoxy-ethanol or DMAC (200 ml) with 10.6 g of 1,9-diiodo-nonane (0.028 moles). A potentiometric iodine titration shows that the reaction has proceeded quantitatively after a relatively short period of time.

Yield: 38 g of 1,9-bis-[N-{3,5-bis-(1,3-dihydroxyisopropylaminocarbonyl)-2,4,6-triiodo-phenyl}-N-hydroxyacetylamino]-nonane, that is, 82% of the theoretical yield.

Melting point: 180°–182° C.
TLC: $R_f$=0.1 Solvent —CH$_2$Cl$_2$/MeOH=2:1
TLC: $R_f$=0.06 Solvent —CHCl$_3$/MeOH/NH$_4$OH (25%)=6:3:1.
C$_{41}$H$_{56}$I$_6$N$_6$O$_{16}$: I calc. 46.14% found 46.58%
Water solubility: ≧100% (w/v) at 25° C.

EXAMPLE 6

1,9-bis-[N-{3,5-bis-(2,3-dihydroxypropylaminocarbonyl)-2,4,6-triiodo-phenyl}-N-(1-α-hydroxypropionyl)-amino]-nonane Formula II: (HO)$_2$C$_3$H$_5$—=HOCH$_2$CH(OH)—CH$_2$—, R=—CH$_3$, alkylene=—(CH$_2$)$_9$—

The potassium salt of 1-5-α-hydroxypropionylamino-2,4,6-triiodo-isophthalic-acid-bis-(2,3-dihydroxypropylamide) (51 g, 0.0625 moles) prepared by reaction of 48.6 g of the free compound with 31.25 ml of 2 N potassium hydroxide, evaporation of the solution formed and drying of the residue, is reacted with 14.4 g of 1,9-diiodo-nonane in 150 ml dimethylsulfoxide.

Yield: 47 g of 1,9-bis-[N-{3,5-bis(2,3-dihydroxypropylaminocarbonyl)-2,4,6-triiodo-phenyl}-N-(1-α-hydroxypropionyl)-amino]-nonane that is, 90% of the theoretical yield.

Melting point: 187° C.
TLC: $R_f$=0.08 and 0.10 Solvent CH$_2$Cl$_2$/MeOH=2:1
C$_{42}$H$_{60}$I$_6$N$_6$O$_{16}$: I calc. 45.36% found 44.99%
[α]$_{436}^{20}$=+38.3° (c=1% in water)
Water solubility: ≧100% (w/v) at 25° C.

EXAMPLE 7

1,8-bis-[N-{3,5-bis-(1,3-dihydroxyisopropylaminocarbonyl)-2,4,6-triiodo-phenyl}-N-(1-α-hydroxypropionyl)-amino]-3,6-dioxa-octane Formula II: (HO)$_2$C$_3$H$_5$—=(HOCH$_2$)$_2$CH—, R=—CH$_3$, alkylene=—CH$_2$CH$_2$—O—CH$_2$CH$_2$—O—CH$_2$CH$_2$—

A solution of 80 g of the sodium salt of IOPAMIDOL (0.1 mole) in 200 ml of DMAC is reacted with 1,8-diiodo-3,6-dioxa-octane (0.051 moles), worked up as described in the preceding examples, purified further by liquid-liquid extraction (water/butanol) and finally crystallized by dissolving it in boiling methanol.

Yield: 54.3 g of 1,8-bis-[N-{3,5-bis-(1,3-dihydroxyisopropylaminocarbonyl)-2,4,6-triiodo-phenyl}-N-(1-α-hydroxypropionyl)-amino]-3,6-dioxa-octane that is, 65% of the theoretical yield.

Melting point: 127°–128° C.
TLC: $R_f$=0.16, 0.23 and 0.30. Solvent CH$_2$Cl$_2$/MeOH=2:1
C$_{40}$H$_{54}$I$_6$N$_6$O$_{18}$: I calc. 45.63% found 45.44%
[α]$_{436}^{20}$=+50.0° (c=1% in water)
Water solubility: 100% (w/v) at 25° C.

EXAMPLE 8

1,11-bis-[N-{3,5-bis-(1,3-dihydroxyisopropylaminocarbonyl)-2,4,6-triiodo-phenyl}-N-(1-α-hydroxypropionyl)-amino]-3,6,9-trioxa-undecane Formula II: (HO)$_2$C$_3$H$_5$—=(HOCH$_2$)$_2$CH—, R=—CH$_3$, alkylene=—CH$_2$CH$_2$—O—CH$_2$CH$_2$—O—CH$_2$CH$_2$—O—CH$_2$CH$_2$—

The sodium salt of IOPAMIDOL (80 g, 0.1 mole) is reacted with 22 g of 1,11-diiodo-3,6,9-trioxa-undecane (0.053 moles).

Yield: 59.7 g of 1,11-bis-[N-{3,5-bis-(1,3-dihydroxyisopropylaminocarbonyl)-2,4,6-triiodo-phenyl}-N-(1-α-hydroxypropionyl)-amino]-3,6,9-trioxa-undecane, that is, 70% of the theoretical yield.

Melting point: 185° C.
TLC: 0.21, 0.29 and 0.34. Solvent: CH$_2$Cl$_2$/MeOH=2:1.
C$_{42}$H$_{58}$I$_6$N$_6$O$_{19}$: I calc. 44.46% found 44.58%
[α]$_{436}^{20}$++43.78° (c=1% in water)
Water solubility: ≧100% (w/v) at 25° C.

EXAMPLE 9

1,5-bis-[N-{3,5-bis-(1,3-dihydroxyisopropylaminocarbonyl)-2,4,6-triiodo-phenyl}-N-(1-α-hydroxypropionyl)-amino]-3-oxa-pentane Formula II: (HO)$_2$C$_3$H$_5$=(HOCH$_2$)$_2$CH—, R=—CH$_3$, alkylene=—CH$_2$CH$_2$—O—CH$_2$CH$_2$—

A solution of 119.9 g of the sodium salt of IOPAMIDOL (0.15 moles) in 210 ml of dimethylsulfoxide is reacted at 20°–25° C. with 28.6 g of 1,5-diiodo-3-oxa-pentane and stirred at room temperature for about 4 to 5 days. The new compound formed is precipitated by mixing the reaction solution with methylene chloride and desalinated by percolation through columns filled with ion-exchange resins.

Yield: 79.8 g of 1,5-bis-[N-{3,5-bis-(1,3-dihydroxypropylamino-carbonyl)-2,4,6-triiodo-phenyl}-N-(1-α-hydroxypropionyl)-amino]-3-oxa-pentane, that is, 65.5% of the theoretical yield.

Melting point: 265° C. with decomposition
TLC: $R_f = 0.34$ Solvent: $CH_2Cl_2/MeOH = 2:1$.
$[\alpha]_D^{20} = +19.67°$, $[\alpha]_{436}^{20} = 43.84°$;
$[\alpha]_{365}^{20} = +81.12°$; c=1% in water,
Solubility: very readily soluble in water, methanol and ethanol.

EXAMPLE 10

1,8-bis-[N-}3,5-bis-(1,3-dihydroxyisopropylaminocarbonyl)-2,4,6-triiodo-phenyl}-N-hydroxyacetylamino]-3,6-dioxa-octane Formula II: $(HO)_2C_3H_5 = (HOCH_2)_2CH—$, $R = —H$,
alkylene = $—CH_2CH_2—O—CH_2CH_2—O—CH_2CH_2—$ A solution of 117.6 g of the sodium salt of 5-hydroxyacetylamino-2,4,6-triiodo-isophthalic-acid-bis-(1,3-dihydroxyisopropylamide) (0.15 moles) in 200 ml of dimethyl sulfoxide is reacted with 28.6 g of 1,8-diiodo-3,6-dioxa-octane and stirred at room temperature for about 3 days until sodium iodide has been formed in an amount calculated for the complete reaction. The new compound is isolated and purified according to the method described in Example 9.

Yield: 92.3 g of 1,8-bis[N-{3,5-bis-(1,3-dihydroxyisopropylaminocarbonyl)-2,4,6-triiodo-phenyl}-N-hydroxy-acetylamino-]-3,6-dioxa-octane that is, 75% of the theoretical yield.

Melting point: 240° C. with decomposition.
TLC: $R_f$ 0.24 and 0.44. Solvent $CHCl_3/MeOH = 1:1$.
Solubility: very readily soluble in water, soluble in boiling methanol and ethanol, slightly soluble in methanol and ethanol at room temperature.

The 5-hydroxyacetylamino-2,4,6-triiodo-isophthalic-acid-bis-(1,3-dihydroxyisopropylamide), used as intermediate, is obtained as follows according to the method described in German Pat. No. 2,547,789:

(A) 5-amino-2,4,6-triiodo-isophthalic acid-dichloride (59.6 g) is reacted in DMAC with 34 g of acetoxyacetyl chloride (0.25 moles), 67.5 g of 5-acetoxyacetylamino-2,4,6-triiodo-isophthalic acid dichloride, melting at 234°-235° C., being obtained.

(B) A solution of 150 g of 4-acetoxyacetylamino-2,4,6-triiodo-isophthalic acid-dichloride in 810 ml of DMAC is reacted first with 80 g of tributylamine and then dropwise with 49.2 g of serinol (=1,3-dihydroxyisopropylamine) in 540 ml of DMAC. A total of 172 g of 5-acetoxyacetylamino-2,4,6-triiodo-isophthalic-acid-bis-(1,3-dihydroxyisopropylamide), which melts at about 190°-192° C. with decomposition is obtained. This compound is suspended in water and treated carefully at 45° C. with 1 N sodium hydroxide at pH 11 until the acetoxy is hydrolyzed completely.

The solution obtained is desalinated by percolation through a cationic exchange resin (Amberlite® IR-120) and anionic exchange resin (Amberlite® IR-45) column. The eluate is evaporated to dryness and taken up in 90% ethanol, the desired intermediate, 5-hydroxyacetylamino-2,4,6-triiodo-isophthalic-acid-bis-(1,3-dihydroxy-isopropylamide) (73 g) being obtained in crystalline form.

Melting point: 300° C. with decomposition.

EXAMPLE 11

1,5-bis-[N-{3,5-bis-(1,3-dihydroxyisopropylaminocarbonyl)-2,4,6-triiodo-phenyl}-N-hydroxyacetyl-amino]-3-oxa-pentane Formula II: $(HO)_2C_5H— = (HOCH_2)_2CH—$, $R = —H$,
alkylene = $—CH_2CH_2—O—CH_2CH_2—$ The sodium salt of 5-hydroxyacetylamino-2,4,6-triiodo-isophthalic-acid-bis-(1,3-dihydroxyisopropylamide) (117.6 g), prepared according to the method described in Example 1, is dissolved in 200 g of dimethyl sulfoxide (DMSO), mixed with 24.5 g of 1,5-diiodo-3-oxa-pentane and stirred for 3 days at room temperature.

After working up the product of the reaction, 75.2 g of the desired compound are obtained, corresponding to a theoretical yield of 63%.

Melting point: 245° C.
TLC: $R_f = 0.27$ Solvent $CHCl_3/MeOH = 1:1$.
$C_{35}H_{46}I_6N_6O_{17}$: I calc. 47.70% found 48.00%
Solubility: this compound is very readily soluble in water, on the other hand, its solubility in methanol and ethanol is limited.

EXAMPLE 12

1,4-bis-[N-{3,5-bis-(1,3-dihydroxyisopropylaminocarbonyl)-2,4,6-triiodo-phenyl}-N-(1-α-hydroxypropionyl)-amino]-2,3-dihydroxybutane Formula II: $(HO)_2C_3H_5 = (HOCH_2)_2CH—$, $R = —CH_3$,
alkylene = $—CH_2—CHOH—CHOH—CH_2—$ A solution of 78.5 g of the sodium salt of IOPAMIDOL (ca. 0.1 mole) in 150 ml of dimethyl sulfoxide is reacted at 20°-25° C. with 16.6 g of 1,4-dibromo-2,3-bis(acetoxy)-butane and stirred for 90-100 hours at room temperature. The reaction can be followed with the help of an argentometric titration of the sodium bromide formed.

When the reaction is completed, the product formed is precipitated by the addition of 250 ml of methylene chloride. The precipitate is dissolved in 500 ml of water and treated carefully at 50° C. with 2 N sodium hydroxide solution at a pH of 10, until the acetoxy functions in the 2,3-position of the alkylene bridge are hydrolyzed off completely.

The solution obtained is desalinated with the help of ion-exchange resins. The desalinated eluate is evaporated. The residue is dissolved in water and the solution forced through a Millipore ® filter (pore size: 0.45 mµ). The filtrate is evaporated to dryness once again. A total of 53 g of the title compound is obtained, corresponding to a yield of 65% in theory.

Melting point: 210°-225° C. with decomposition.
$C_{38}H_{50}I_6N_6O_{18}$: I calc. 46.42% found 46.25%
Water solubility: $\geq 100\%$ (w/v) at 25° C.

EXAMPLE 13

1,5-bis-[N-{3,5-bis-(2,3-dihydroxypropylaminocarbonyl)-2,4,6-triiodo-phenyl}-N-hydroxyacetyl-amino]-3-oxa-pentane Formula II: $(OH)_2C_3H_5 = HOCH_2—CHOH—CH_2—$,
$R = —H$, alkylene = $—CH_2CH_2—O—CH_2CH_2—$ The sodium salt of 5-hydroxyacetylamino-2,4,6-triiodo-isophthalic-acid-bis-(2,3-dihydroxypropylamide) (117.6 g), prepared as in Example 1, is reacted in 200 g of DMSO with 24.5 g of 1,5-diiodo-3-oxa-pentane as in Example 11. After working up the product, the title compound is obtained in a yield of 82.0 g, corresponding to 68% of the theoretical yield.

Melting point: >200° C. with decomposition.

TLC: $R_f$=0.15. Solvent CHCl$_3$/MeOH=1:1.

$C_{36}H_{46}I_6N_6O_{17}$: I calc. 47.70% found 47.48%.

This compound is very readily soluble in cold water, soluble in boiling methanol but only slightly soluble in cold methanol and in ethanol.

The 5-hydroxyacetylamino-2,4,6-triiodo-isophthalic-acid-bis-(2,3-dihydroxypropylamide), used as an intermediate, is obtained by the method described in German Pat. No. 2,457,789 as follows:

A solution of 24.4 g of 5-acetoxyacetylamino-2,4,6-triiodo-isophthalic acid dichloride (0.035 moles) in 60 ml of DMAC is added dropwise and with stirring to a solution of 15.9 g of 2,3-dihydroxypropylamine (=1-amino-2,3-dihydroxy-propane) (0.175 moles) in 100 ml of DMAC.

An oily 5-acetoxyacetylamino-2,4,6-triiodo-isophthalic-acid-bis-(2,3-dihydroxypropylamide) is obtained. The compound is taken up in 250 ml of water and treated carefully at 40° C. with 1 N sodium hydroxide until the acetoxy group is hydrolyzed off completely.

The solution obtained is desalinated by percolation through a column of cationic exchange resin (Amberlite ® IR-120) and then through a column of anionic exchange resin (Amberlite ® IR-45). The eluate is evaporated to dryness. After some time, crystallization takes place. The desired intermediate, 5-hydroxyacetylamino-2,4,6-triiodo-isophthalic-acid-bis-(2,3-dihydroxypropylamide) (19.4 g) is obtained in pure form by recrystallization from a small amount of water.

Melting point: 290° C.

TLC: $R_f$=0.24 Solvent: ethyl acetate/ethanol/ammonia (25%)=15:7:6.

$C_{16}H_{20}I_3N_3O_8$: C calc. 25.18%, found 25.01%. I calc. 49.89%, found 49.75%.

EXAMPLE 14

1,8-bis-[N-{3,5-bis-(2,3-dihydroxypropylaminocarbonyl)-2,4,6-triiodo-phenyl}-N-hydroxyacetylamino]-3,6-dioxa-octane Formula II:
(HO)$_2$C$_3$H$_5$—=HOCH$_2$—CH(OH)—CH$_2$—, R=—H, alkylene=—CH$_2$CH$_2$OCH$_2$CH$_2$OCH$_2$CH$_2$—

The sodium salt of 5-hydroxyacetylamino-2,4,6-triiodo-isophthalic-acid-bis-(2,3-dihydroxypropylamide) (117.5 g, 0.15 moles) is reacted with 28.6 g (0.075 moles) of 1,8-diiodo-3,5-dioxa-octane, as in Example 11. A total of 73.5 g of the title compound is obtained, corresponding to a yield of 60%.

Melting point: ≧200° C. with decomposition.

TLC: $R_f$=0.14. Solvent: chloroform/methanol=1:1.

$C_{38}H_{50}I_6N_6O_{18}$: I calc. 46.42% found 46.65%

This compound is very readily soluble in cold water, readily soluble in boiling methanol, but only somewhat soluble in cold methanol and in boiling ethanol.

EXAMPLE 15

1,3-bis-[N-{3,5-bis-(2,3-dihydroxypropylaminocarbonyl)-2,4,6-triiodo-phenyl}-N-hydroxyacetylamino}-propane Formula II: (HO)$_2$C$_3$H$_5$—=HOCH$_2$—CHOH—CH$_2$, R=—H, alkylene=—CH$_2$—CH$_2$—CH$_2$—

The sodium salt of 5-hydroxyacetylamino-2,4,6-triiodo-isophthalic-acid-bis-(2,3-dihydroxypropylamide) (52.3 g, 0.067 moles) is dissolved at 45° C. in 150 ml of DMAC, treated at room temperature with 6.75 g of 1,3-dibromopropane (0.034 moles) and stirred for some hours until the reaction is completed. The product is worked up according to the method described in Example 1.

A total of 37.2 g of the title compound is obtained, corresponding to a theoretical yield of 71.2%.

Melting range: 234°-236° C. with decomposition.

TLC: $R_f$=0.27. Solvent: 2-butanol/AcOH/H$_2$O=15:3:5.

$C_{35}H_{44}I_6N_6O_{16}$: I calc. 48.61%, found 48.26%.

This compound is very readily soluble in water (100% (w/v) at 25° C.), somewhat soluble in methanol (3.3%) and slightly soluble in ethanol and chloroform.

EXAMPLE 16

1,3-bis-[N-{3,5-bis-(1,3-dihydroxyisopropylaminocarbonyl)-2,4,6-triiodo-phenyl}-N-(1-α-hydroxypropionyl)-amino]-propane Formula II: (HO)$_2$C$_3$H$_5$—=(HOCH$_2$)$_2$CH—, R=—CH$_3$, alkylene=—CH$_2$—CH$_2$—CH$_2$—

A solution of 59.9 g of the sodium salt of IOPAMIDOL (0.075 moles) in 105 g of DMSO is reacted at room temperature with 11.5 g of 1,3-diiodopropane (0.0375 moles).

The title compound is obtained in a yield of 31 g, corresponding to a theoretical yield of 52%.

Melting range: 280° C.

TLC: $R_f$=0.29. Solvent: methylene chloride/methanol=2:1

$C_{37}H_{48}I_6N_6O_{16}$: I calc. 47.76%, found 47.54%.

The compound is very readily soluble in water (100% (w/v) at 25° C.), easily soluble in methanol (25% (w/v) at 25° C. and 100% (w/v) at the boiling point) but only very slightly soluble in ethanol (1% at 25° C.) and practically insoluble in chloroform.

EXAMPLE 17

1,7-bis-[N-{3,5-bis-(2,3-dihydroxypropylaminocarbonyl)-2,4,6-triiodo-phenyl}-N-hydroxyacetyl-amino]-4-oxa-heptane Formula II:
(HO)$_2$C$_3$H$_5$—=HOCH$_2$—CHOH—CH$_2$—, R=—H, alkylene=—CH$_2$CH$_2$CH$_2$OCH$_2$CH$_2$CH$_2$—

A solution of 125.5 g of the sodium salt of 5-hydroxyacetylamino-2,4,6-triiodo-isophthalic-acid-bis-(2,3-dihydroxypropylamide) (0.16 moles) in 210 g of DMSO are reacted with stirring and at room temperature with 28.4 g of 1,7-diiodo-4-oxa-heptane.

The title compound is obtained in a yield of 104 g, corresponding to 80% of the theoretical yield.

Melting range: sinters at 225° C., decomposes at 250° C.

TLC: $R_f$=0.15. Solvent: chloroform/methanol=1:1.

$C_{38}H_{50}I_6O_{17}$: I calc. 46.88%, found 46.55%.

The compound is very readily soluble in water, slightly soluble in cold methanol and very slightly soluble in ethanol.

EXAMPLE 18

1,7-bis-[N-{3,5-bis-(1,3-dihydroxyisopropylaminocarbonyl)-2,4,6-triiodo-phenyl}-N-(1-α-hydroxypropionyl)-amino]-4-oxa-heptane Formula II: $(HO)_2C_3H_5{-}{=}(HOCH_2)_2CH{-}$,
$R = {-}CH_3$,
alkylene $= {-}CH_2CH_2CH_2{-}O{-}CH_2CH_2CH_2{-}$ A solution of 56 g of the sodium salt of IOPAMIDOL (0.07 moles) in 100 g of DMSO is reacted at room temperature with 12.4 g of 1,7-diiodo-4-oxa-heptane (0.035 moles) until the theoretically required amount of sodium iodide has been formed after more than 90 hours. The course of the reaction can be followed by titrating aliquot samples with silver nitrate.

The title compound is obtained in a yield of 36.7 g, corresponding to 63.5% of the theoretical yield.

Melting point range: sinters at 228° C., decomposes at 255° C.

TLC: $R_f=0.16$ and 0.24. Solvent: methylene chloride/methanol=2:1.

$C_{40}H_{54}I_6N_6O_{17}$: I calc. 46.08% found 45.74%.

$[\alpha]_D^{20} = +17.9°$, $[\alpha]_{436}^{20} = +41.4°$ (c=1.021% in water).

This compound is very readily soluble in water, readily soluble in methanol, but only slightly soluble in ethanol.

EXAMPLE 19

1,16-bis-[N-bis{3,5-bis-(2,3-dihydroxypropylaminocarbonyl)-2,4,6-triiodo-phenyl}-N-hydroxyacetyl-amino]-4,7,10,13-tetraoxa-hexadecane Formula II:
$(HO)_2C_3H_5{-}{=}HOCH_2{-}CHOH{-}CH_2{-}$, $R={-}H$,
alkylene $= {-}CH_2CH_2CH_2{-}(OCH_2CH_2{-})_3{-}O{-}CH_2CH_2CH_2{-}$ A solution of 39.25 g of the sodium salt of 5-hydroxyacetylamino-2,4,6-triiodo-isophthalic-acid-bis-(2,3-dihydroxypropylamide) (0.05 moles) in 60 g of DMSO is reacted at room temperature with stirring with 12.16 g of 1,16-diiodo-4,7,10,13-tetraoxa-hexadecane (0.025 moles) until the theoretical amount of sodium iodide has been formed.

The title compound is obtained in a yield of 35 g, corresponding to 79% of the theoretical.

Melting point: 176°–180° C.

TLC: $R_f=0.18$ Solvent: chloroform/methanol=1:1

$C_{44}H_{62}I_6N_6O_{20}$: I calc. 43.45% found 43.65%

This compound is very readily soluble in water (≥100% (w/v) at 20° C.), easily soluble in methanol (12% (w/v)), slightly soluble in ethanol and very slightly soluble in chloroform.

EXAMPLE 20

1,16-bis-[N-{3,5-bis-(1,3-dihydroxyisopropylaminocarbonyl)-2,4,6-triiodo-phenyl}-N-(1-α-hydroxypropionyl)-amino]-4,7,10,13-tetraoxa-hexadecane Formula II: $(HO)_2C_3H_5{-}{=}(OHCH_2)_2CH{-}$,
$R={-}CH_3$,
alkylene $= {-}CH_2CH_2CH_2{-}(OCH_2CH_2{-})_3{-}O{-}CH_2CH_2CH_2{-}$ A solution of 40 g of sodium salt of IOPAMIDOL (0.05 moles) in 60 g of DMSO is reacted at 20°–25° C. with stirring with 12.16 g of 1,16-diiodo-4,7,10,13-tetraoxa-hexadecane (0.025 moles) until the theoretical amount (0.05 moles) of sodium iodide has been formed.

The title compound is obtained in a yield of 33.7 g, corresponding to 75% of the theoretical.

Melting point: 196°–199° C.

TLC: $R_f=0.28$ and 0.35. Solvent: chloroform/methanol=2:1

$C_{44}H_{66}I_6N_6O_{20}$: I calc. 42.67% found 42.12%.

$[\alpha]_D^{20} = +15.6°$, $[\alpha]_{436}^{20} = +37.5°$ (c=1.023% in water)

This compound is very soluble in water (≥100% (w/v) at 20° C.), readily soluble in methanol, soluble in ethanol, but only slightly soluble in chloroform.

EXAMPLE 21

1,3-bis-[N-{3,5-bis-(r(+) 2,3-dihydroxypropylaminocarbonyl)-2,4,6-triiodo-phenyl}-N-hydroxyacetylamino]-propane Formula II:
$(HO)_2C_3H_5{-}{=}r(+)HOCH_2{-}CHOH{-}CH_2{-}$,
$R={-}H$, alkylene $= {-}CH_2CH_2CH_2{-}$ This compound is synthesized in exactly the same manner as the racemic compound described in Example 15.

Melting point range: sinters at 224° C., decomposes at 240° C.

$[\alpha]_D^{20} = +3.8°$, $[\alpha]_{436}^{20} = +9.2°$ (c=5% in water)

The other properties are identical with those of the racemic compound.

The starting material required, 5-hydroxyacetylamino-2,4,6-triiodo-isophthalic-acid-bis-(r(+)2,3-dihydroxypropylamide) is obtained by a method similar to that described for the racemic compound in Example 13.

A solution of 63.5 g of 5-acetoxyacetylamino-2,4,6-triiodo-isophthalic acid dichloride in 90 ml of DMAC is added dropwise to a solution of 22 g of r(+)2,3-dihydroxypropylamine (0.242 moles) in 45 ml of DMAC in which 30.6 g of potassium carbonate (0.219 moles) are suspended. Stirring is continued for 20 hours at room temperature. The further treatment and working up to the desired 5-hydroxyacetylamino-2,4,7-triiodo-isophthalic-acid-bis-(r(+)2,3-dihydroxypropylamide) is identical with that described in Example 13. The yield is 51.84 g, corresponding to 75% of the theoretical.

TLC: $R_f=0.22$, solvent: ethyl acetate/glacial acetic acid/water=20:10:6

$C_{16}H_{30}I_3N_3O_8$: I calc. 49.89% found 50.04%.

Utilization:

Of the compounds described in the preceding examples, the bis-[N-{3,5-bis-(2,3-dihydroxypropylaminocarbonyl)-2,4,6-triiodo-phenyl}-N-hydroxyacetyl-amino]-alkanes are generally preferred. They are comparatively simpler and more inexpensively accessible than the 1,3-dihydroxyisopropyl derivatives, especially when these have, in addition, α-hydroxypropionyl residues at the aromatic nitrogen atom.

The water solubility of the preferred compounds, which have 2,3-dihydroxypropyl and hydroxyacetyl residues, is practically unlimited. The compounds are stable. All physical, chemical and pharmacological prerequisites for use in X-ray contrasting materials for neuroradiology, especially for the visualization of cavities which contain the cerebrospinal fluid, are fulfilled particularly well by these compounds.

The low osmolality of the inventively obtained compounds, which is significantly lower than that of the previously, actually used nonionic X-ray contrasting materials METRIZAMIDE and IOPAMIDOL is an important property. Also important is the increased viscosity of the new contrasting materials, which prevents premature drainage of the contrasting material from the inspection space, particularly in the case of neuroradiology, and makes better contrast photographs possible.

In the following tables, the osmolality, osmotic pressure and viscosity of three inventively obtained compounds A, B and C are compared with the two most important and comparable, previously known, nonionic X-ray contrasting materials D and E.

In the tables:

A = 1,3-bis-[N-{3,5-bis-(2,3-dihydroxypropylaminocarbonyl)-2,4,6-triiodo-phenyl}-N-hydroxyacetyl-amino]-propane (Example 15);

B = 1,5-bis[N-{3,5-bis-(2,3-dihydroxypropylaminocarbonyl)-2,4,6-triiodo-phenyl}-N-hydroxyacetyl-amino]-3-oxa-pentane (Example 13);

C = 1,16-bis-[N-{3,5-bis-(2,3-dihydroxy-propylaminocarbonyl)-2,4,6-triiodo-phenyl}-N-hydroxyacetyl-amino]-4,7,10,13-tetraoxa-hexadecane (Example 19);

D = 1,5-α-hydroxypropionylamino-2,4,6-triiodo-isophthalic-acid-bis-(1,3-dihydroxyisopropylamide) (International non-proprietary name = IOPAMIDOL);

E = 3-acetylamino-5-N-methyl-acetylamino-2,4,6-triiodo-benzoyl-glucosamine (International non-proprietary name = METRIZAMIDE).

TABLE 1

| Compound | mg I/ml | Osmolality (mOsm/kg) 37° C. | Osmotic Pressure atm 37° C. |
|---|---|---|---|
| A | 250 | 160 | 3.93 |
|   | 300 | 184 | 4.67 |
|   | 350 | 219 | 5.57 |
| B | 250 | 199 | 5.06 |
|   | 300 | 240 | 6.11 |
|   | 350 | 283 | 7.21 |
| C | 250 | 204 | 5.21 |
|   | 300 | 269 | 6.84 |
|   | 350 | 364 | 9.26 |
| D | 250 | 514 | 13.09 |
|   | 300 | 619 | 15.76 |
|   | 350 | 737 | 18.77 |
| E | 300 | 485 |  |

The osmotic pressure of compounds A and B is less even at the highest concentrations than that of the body fluids blood = 7.7). With respect to their osmotic pressure, mixtures of A, B and/or C may be matched exactly to the osmotic pressure of the body fluids and may therefore be administered to the organism with the least discomfort.

This permits the safe usage of even the highest dosages of X-ray contrasting materials, which are so very much desired by radiologists in order to improve the radio-opacity and therefore the information provided by X-ray photographs.

TABLE 2

| Compound | °C. | Viscosity in Centipoise (cP) of Aqueous Solutions Containing | |
|---|---|---|---|
| | | 300 mg I/ml | 350 mg I/ml |
| A | 20 | 20.7 | 47.8 |
|   | 37 | 7.4 | 17.3 |
| B | 20 | 19.5 | 38.5 |
|   | 37 | 7.6 | 18.9 |
| C | 20 | 31.1 | 113.7 |

TABLE 2-continued

| Compound | °C. | Viscosity in Centipoise (cP) of Aqueous Solutions Containing | |
|---|---|---|---|
| | | 300 mg I/ml | 350 mg I/ml |
|   | 37 | 16.5 | 34.9 |
| D | 20 | 8.95 |  |
|   | 37 | 4.70 |  |
| E | 20 | 11.7 |  |
|   | 37 | 5.98 |  |

Diffusion of the X-ray contrasting materials too rapidly is undesirable. With the inventive compounds, dilution of the contrast is prevented by the comparatively high viscosity of the new X-ray contrasting materials.

The new bis-[N-{3,5-bis-(hydroxyalkylaminocarbonyl)-2,4,6-triiodo-phenyl}-N-(α-hydroxyacyl)-amino]-alkanes of the general formula (I) are used predominantly in the form of their aqueous solutions.

Depending on their intended application, ca. 15% to ca. 70% solutions (w/v) (100% = 100 g of contrasting material per 100 ml of solution), containing from about 60 to about 350 mg of iodine per ml, are used. The more concentrated solutions are preferred. The nature of the application depends on the vessel which is to be made visible.

For myelography and radiculography, the solutions are instilled after lumbar or suboccipital puncture. In the case of ventriculography, the ventricles are punctured directly.

| Dosage: | |
|---|---|
| myeolograph | ca. 5–15 ml |
| radiculography | ca. 3–5 ml |
| ventribulography | ca. 1–2 ml |

The preparation of solutions of X-ray contrasting materials is simple, because it is unnecessary to prepare any salt solutions.

For example, the pure 2,4,6-triiodo-isophthalic acid amides, obtained according to the preceding examples, are dissolved in the desired amount of doubly distilled water under sterile conditions, filtered, filled into serum bottles or ampoules and subsequently sterilized. The triiodo-isophthalic acid amides of this invention are not decomposed by heat sterilization.

EXAMPLE 22

Injection solution containing
1,3-bis-[N-{3,5-bis-(2,3-dihydroxypropylaminocarbonyl)-2,4,6-triiodo-phenyl}-N-hydroxyacetyl-amino]-propane = Compound A Procedure:

The sodium-calcium salt of ethylenediaminetetraacetic acid, tromethamine, and the contrasting material are dissolved in doubly distilled water. If necessary, the pH of the solution is adjusted to ca. 7 by the addition of 1 N hydrochloric acid. The volume is made up to 20 ml. The solution is filtered using a membrane filter of 0.45 mμ. The filtrate is filled into ampoules and sterilized for 30 minutes at 120° C.

The following table sets forth the actual compositions of the solutions and their viscosities.

| Composition of 20 ml | | Iodine Content of Injection Solutions in mg/ml | | |
|---|---|---|---|---|
| Aliquots of solution | | 200 | 300 | 420 |
| Compound A | g | 8.23 | 12.34 | 14.40 |
| Disodium-calcium salt of ethylenediamine-tetra-acetic acid hexahydrate | mg | 5.2 | 7.8 | 9.0 |
| Tromethamine [tris-(hydroxymethyl)-amino-methane] | mg | 11.4 | 17.1 | 20 |
| Doubly distilled water to | ml | 20 | 20 | 20 |
| Density at 37° C. | | 1.208 | 1.319 | 1.371 |
| Viscosity at 37° C. | cP | 2.5 | 7.4 | 47.8 |

(cP = centipoise)

EXAMPLE 23

Injection Solution containing Compounds A and C:

| | |
|---|---|
| Compound A (see Example 15) | 50 g |
| Compound C (see Example 19) | 26.7 g |
| Sodium carbonate | 0.4 g |
| Disodium salt of ethylenediamineacetic acid | 0.02 g |
| Doubly distilled water to a volume of | 100 ml |

Procedure:

The components are combined and made up to 125 ml with doubly distilled water, filtered, filled into ampoules under hygienically satisfactory conditions and subsequently sterilized. Iodine content: 350 mg/ml.

EXAMPLE 24

Infusion Solution

| | |
|---|---|
| Compound A (see Example 15) | 205.72 g |
| Sodium carbonate | 0.5 g |
| Disodium salt of ethylenediamine-tetra-acetic acid | 0.03 g |
| Doubly distilled water to a volume of | 500 ml |

Procedure:

The components are combined, diluted to 500 ml, filtered and filled under nitrogen into 2 infusion flasks and sterilized.

Iodine content: 200 mg/ml
Viscosity: 4.1 cP at 20° C.

EXAMPLE 25

Injection Solution

| | |
|---|---|
| 1,5-bis-[N-{3,5-bis-(1,3-dihydroxyisopropylamino-carbonyl)-2,4,6-triiodo-phenyl}-N-hydroxyacetyl-amino]-3-oxa-pentane (see Example 13) | 60.13 g |
| Disodium-calcium salt of ethylenediamine-tetra-acetic acid.6H₂O | 40 mg |
| Tromethamine | 47 mg |
| Doubly distilled water to | 100 ml |

Procedure: As in Example 22.
Iodine content: 300 mg/ml.

What is claimed is:

1. Bis-[N-{3,5-bis-(hydroxyalkylaminocarbonyl)-2,4,6-triiodo-phenyl}-N-(α-hydroxyacyl]-alkanes having the formula (I)

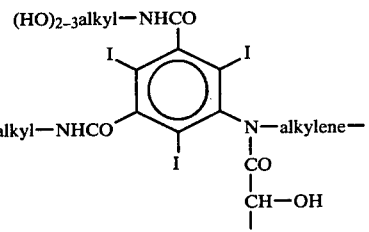

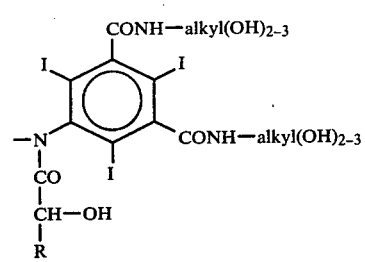

wherein
(HO)₂₋₃alkyl is 1,3-dihydroxyisopropyl, 2,3-dihydroxypropyl, or 1,3-dihydroxy-2-hydroxymethylisopropyl,
R is hydrogen or methyl, and
alkylene is a bivalent alkylene residue with 2 to 10 carbon atoms which may be substituted by hydroxy functions, or a mono-, di-or poly-oxa-alkylene residue with 4 to 12 carbon atoms, which may be substituted by hydroxy functions.

2. The compound of claim 1 wherein the alkylene is

wherein x is 2–10, y is 1–4, and n is 2 or 3.

3. Bis-[N-{3,5-bis(dihydroxypropylaminocarbonyl)-2,4,6-triiodo-phenyl}-N-(α-hydroxyacyl)-amino]-alkanes having the formula (I)

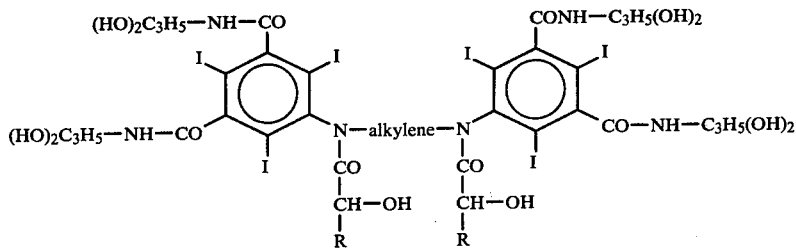

in which
(HO)₂C₃H₅— is 1,3-dihydroxyisopropyl or 2,3-dihydroxypropyl,
R is hydrogen or methyl, and alkylene is a bivalent alkylene residue with 2 to 10 carbon atoms which may be substituted by hydroxy functions, or a mono-, di- or poly-oxa-alkylene residue with 4 to 12 carbon atoms which may also be substituted by hydroxy functions.

4. The compound of claim 3 wherein the alkylene is

—(CH$_2$)$_x$ or (C$_n$H$_{2n}$O)$_y$—C$_n$H$_{2n}$ wherein x is 2–10, y is 1–4, and n is 2 or 3.

5. An X-ray contrasting composition comprising a pharmacologically acceptable carrier and a radio-opaque effective amount of bis-[N-{3,5-bis-(hydroxyalkylaminocarbonyl)-2,4,6,-triiodo-phenyl}-N-(α-hydroxyacyl)-amino]-alkane having the formula (I)

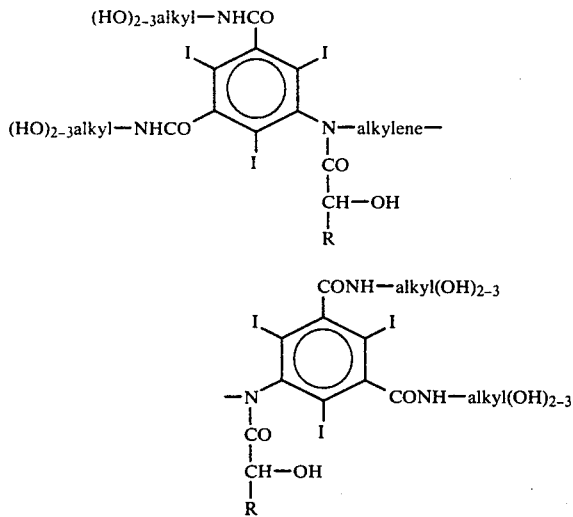

wherein
(HO)$_{2-3}$alkyl is 1,3-dihydroxyisopropyl, 2,3-dihydroxypropyl or 1,3-dihydroxy-2-hydroxymethylisopropyl,
R is hydrogen or methyl, and
alkylene is a bivalent alkylene residue with 2 to 10 carbon atoms which may be substituted by hydroxy functions, or a mono-, di-, or poly-oxa-alkylene residue with 4 to 12 carbon atoms which may be substituted by hydroxy functions.

6. In a method for enhancement of the visualization of vessels in a patient wherein an X-ray contrasting composition is injected into the vessel, the improvement which comprises said X-ray contrasting composition comprising a radio-opaque effective amount of

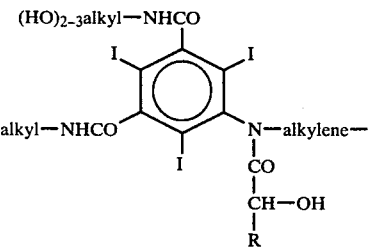

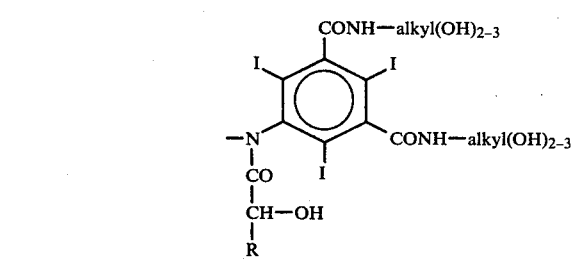

wherein
(HO)$_{2-3}$alkyl is 1,3-dihydroxyisopropyl, 2,3-dihydroxypropyl, or 1,3-dihydroxy-2-hydroxymethylisopropyl,
R is hydrogen or methyl, and
alkylene is a bivalent alkylene residue with 2 to 10 carbon atoms which may be substituted by hydroxy functions, or a mono-, di- or poly-oxa-alkylene residue with 4 to 12 carbon atoms which may be substituted by hydroxy functions,
and a carrier.

7. 1,3-bis[N-{3,5-bis-(2,3-dihydroxypropylaminocarbonyl)-2,4,6-triiodo-phenyl}-N-hydroxyacetyl-amino]-propane.

* * * * *

UNITED STATES PATENT OFFICE
CERTIFICATE OF CORRECTION

Patent No. 4,348,377    Dated September 7, 1982

Inventor(s) Ernst Felder and Davide Pitre

It is certified that error appears in the above-identified patent and that said Letters Patent are hereby corrected as shown below:

On the title page, Item (54) should read as follows:

--[54] New Derivatives Of 2,4,6-Triiodo-Isophthalic Acid, Processes For Their Synthesis and X-Ray Contrasting Materials Containing These --

Signed and Sealed this

Twenty-sixth Day of October 1982

[SEAL]

Attest:

GERALD J. MOSSINGHOFF

Attesting Officer    Commissioner of Patents and Trademarks